United States Patent
Dennis

(10) Patent No.: US 7,658,195 B2
(45) Date of Patent: Feb. 9, 2010

(54) MALE INCONTINENCE CONTROL DEVICE

(75) Inventor: William G. Dennis, Jacksonville, FL (US)

(73) Assignee: Gyrx, Inc., Jacksonville, FL (US)

( * ) Notice: Subject to any disclaimer, the term of this patent is extended or adjusted under 35 U.S.C. 154(b) by 101 days.

(21) Appl. No.: 11/564,492

(22) Filed: Nov. 29, 2006

(65) Prior Publication Data

US 2008/0121241 A1    May 29, 2008

(51) Int. Cl.
*A61F 5/37* (2006.01)
*A61F 5/48* (2006.01)
*A61F 5/00* (2006.01)

(52) U.S. Cl. ............... 128/885; 128/893; 128/886; 128/DIG. 25; 600/38; 600/41

(58) Field of Classification Search ............ 128/883, 128/885–886, DIG. 24, DIG. 25; 600/29–31, 600/38, 41
See application file for complete search history.

(56) References Cited

U.S. PATENT DOCUMENTS

| | | | | |
|---|---|---|---|---|
| 3,147,754 A | * | 9/1964 | Koessler ............... | 128/885 |
| 3,176,551 A | * | 4/1965 | Hansen ................ | 81/423 |
| 3,203,421 A | * | 8/1965 | Bialick ................ | 128/885 |
| 3,866,611 A | * | 2/1975 | Baumrucker ........... | 128/885 |
| 5,571,125 A | * | 11/1996 | Chadwick ............. | 606/157 |
| 6,463,932 B1 | * | 10/2002 | Single et al. .......... | 128/885 |
| 6,827,085 B2 | | 12/2004 | Single et al. | |
| 6,904,916 B2 | | 6/2005 | Bakane | |
| 6,981,505 B2 | * | 1/2006 | Krause et al. .......... | 128/885 |
| 2005/0256365 A1 | | 11/2005 | Timm et al. | |

\* cited by examiner

*Primary Examiner*—Patricia Bianco
*Assistant Examiner*—Brandon Jackson
(74) *Attorney, Agent, or Firm*—Hunton & Williams

(57) ABSTRACT

A male urinary incontinence control device comprising dorsal and ventral arms is presented. The dorsal clamping portion is configured for engaging a dorsal surface of a user's penis. The ventral clamping portion is configured for engaging a ventral surface of a user's penis. The device also comprises an adjustable hinge connecting the hinge end of the dorsal arm clamping portion to the hinge end of the ventral arm clamping portion. The adjustable hinge comprises a pivot fixed to one of the ventral and dorsal arms and about which the other of the ventral and dorsal arms can be selectively rotated between a closed position wherein the dorsal arm clamping portion is in opposition with the ventral arm clamping portion and an open position. The location of the pivot relative to the other of the ventral and dorsal arms is selectively adjustable to establish a desired spacing between the ventral and dorsal arms when in the closed position.

18 Claims, 6 Drawing Sheets

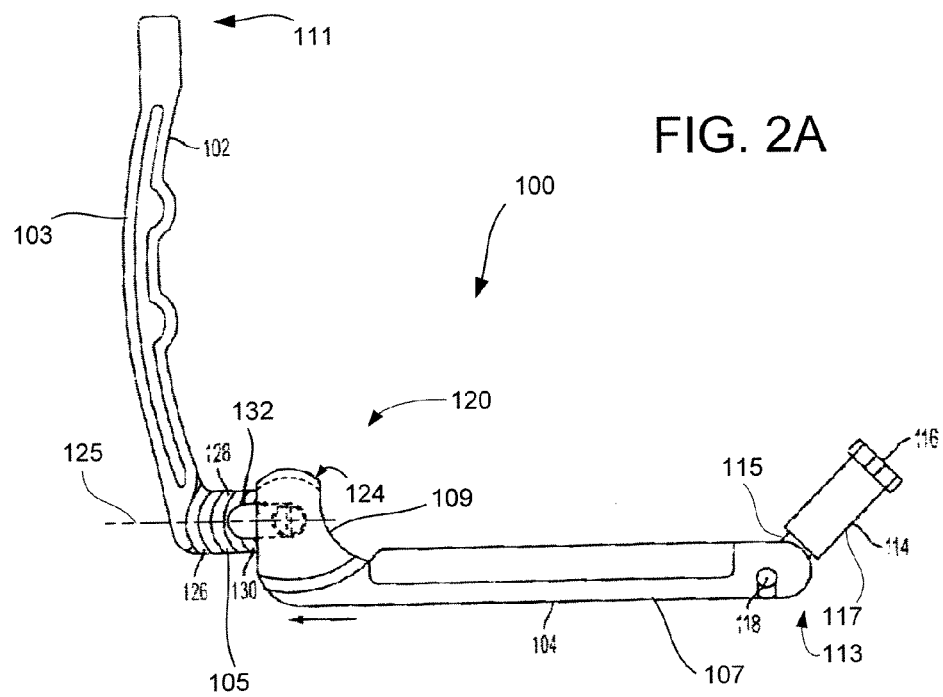
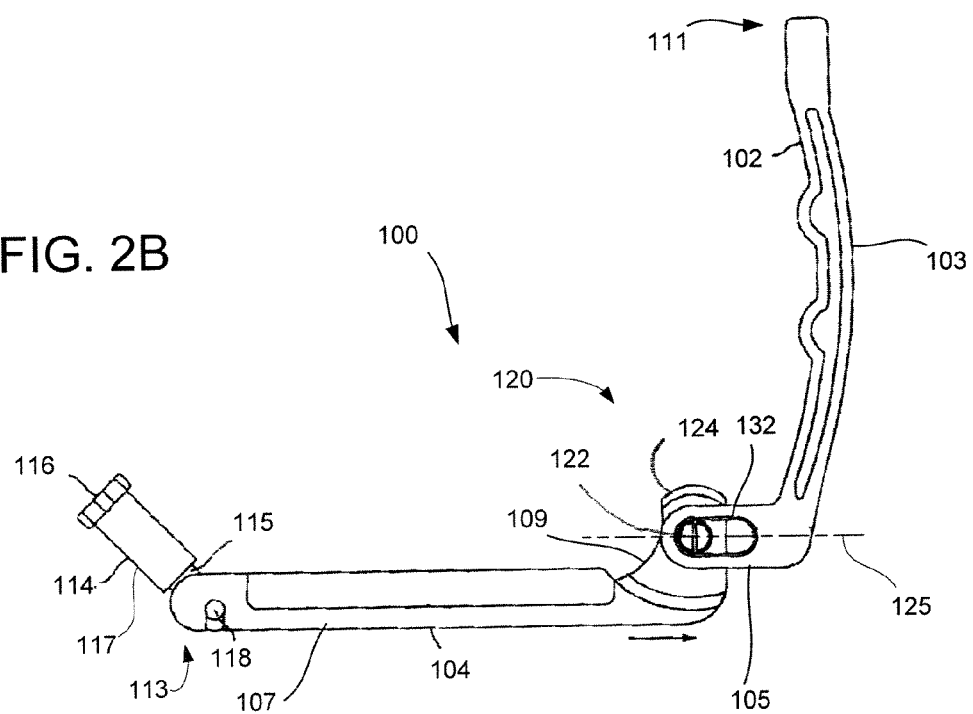

US 7,658,195 B2

MALE INCONTINENCE CONTROL DEVICE

FIELD OF THE INVENTION

The present invention relates to devices used to control urinary incontinence of a male patient. The scope of the present invention includes external incontinency devices that are clamped or affixed to a male's penis to aid in restricting urine flow through the urethra.

BACKGROUND OF THE INVENTION

Urinary incontinence is the involuntary excretion of urine from one's body. In many instances the release results from one or more underlying medical conditions. Male incontinence is a problem that results in distress, embarrassment and inconvenience for many men suffering from the involuntary excretion of urine. To deal with this problem, invasive procedures are sometimes used. In other circumstances, non-invasive devices have been created to address male incontinence, such as diapers and penis restricting mechanisms.

The urethra is a tube which connects the urinary bladder to the outside of the body for purposes of excreting urine. In the human male, the urethra is typically about 20 cm (7.9 inches) long and opens at the end of the penis. Along this tract, the final portion of the urethra leading to the outside is commonly known as the spongy urethra (or penile urethra). This section runs along the length of the penis on its ventral (underneath) surface. Although varying, it is normally about 15-16 cm (5.9-6.3 inches) in length, and travels through the corpus spongiosum.

Generally, the goal of penis restriction devices is to somehow close, or partially restrict flow through, the urethra at some area along the spongy urethra. This in turn helps prevent the involuntary excretion of urine. Due to the unique anatomy of a penis, these external restriction devices that are clamped or otherwise secured to a penis can be effective in controlling urine flow through the spongy urethra. A given level of pressure applied to the spongy urethra will collapse or narrow the passageway and prevent or reduce urine from flowing through. These restriction devices have been used in the art to prevent involuntary voiding of a bladder and accordingly to prevent urine leakage.

Existing restriction devices can generally be divided into encirclement devices that typically have relatively flexible members designed to surround the penis shaft and clamp devices that typically have rigid or semi-rigid hinged clamping members. While many of these devices allow for a certain degree of adjustability, they do not account for the myriad variations in cross-sectional shape that may be encountered. The result may be user discomfort or inadequate or misplaced application of pressure and consequent leakage.

SUMMARY OF THE INVENTION

The present invention provide an improved male urinary incontinence control device that is more comfortable for users because of its unique adjustment and tuning capabilities. An illustrative embodiment of the invention provides a male urinary incontinence control device comprising a dorsal arm comprising a dorsal clamping portion having a hinge end and a free end. The dorsal clamping portion is configured for engaging a dorsal surface of a user's penis. The device further comprises a ventral arm comprising a ventral clamping portion having a hinge end and a free end. The ventral clamping portion is configured for engaging a ventral surface of a user's penis. The device also comprises an adjustable hinge connecting the hinge end of the dorsal arm clamping portion to the hinge end of the ventral arm clamping portion. The adjustable hinge comprises a pivot fixed to one of the ventral and dorsal arms and about which the other of the ventral and dorsal arms can be selectively rotated between a closed position wherein the dorsal arm clamping portion is in opposition with the ventral arm clamping portion and an open position. The location of the pivot relative to the other of the ventral and dorsal arms is selectively adjustable to establish a desired spacing between the ventral and dorsal arms when in the closed position. The device still further comprises a latch attached to at least one of the ventral arm and the dorsal arm and configured for selectively securing the free end of the dorsal arm to the free end of the ventral arm when the ventral and dorsal arms are in the closed position.

BRIEF DESCRIPTION OF THE DRAWINGS

FIG. 2A depicts a left side view of the device of FIG. 1A in an open configuration;

FIG. 2B depicts a right side view of the device of FIG. 1A in the same configuration as in FIG. 2A;

DETAILED DESCRIPTION OF THE INVENTION

Figure 1A:
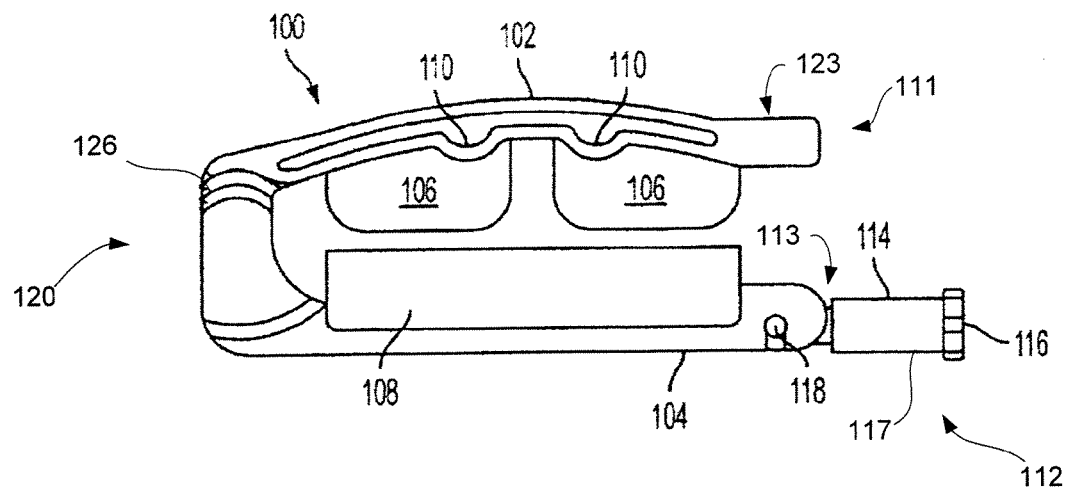
FIG. 1A depicts a left side view of a male incontinence device according to an embodiment of the invention in a closed but unlatched configuration.

The present invention provides a clamp-type male urinary incontinence control device that provides additional adjustment capability that accounts for variations in minor axis diameter and overall girth of a user's penis. This adjustability results in added comfort and improved performance through the application of more direct pressure upon the urethra and through reduced pressure upon the critical blood vessels running through the penis. When properly used, the enhanced adjustment capabilities can reduce leakage of urine through the urethra and improve blood flow throughout the penis.

The basic device of the invention is a clamp-type device having dorsal and ventral arms connected at an adjustable pivot. The dorsal arm is configured so that when the device is properly secured to the penis, pressure is applied so as to constrict the urethra, thereby reducing or preventing urinary flow. In some embodiments the dorsal arm may comprise projections extending inwardly from the dorsal arm. Such embodiments may achieve another purpose of the invention by improving overall circulation of blood through the reduction of pressure upon certain blood vessels or veins running through the penis. Both the dorsal and ventral arms may have cushioning material on their opposing surfaces for engaging the dorsal and ventral surfaces of the penis, respectively.

The control devices of the invention may be put onto the penis by opening the dorsal arm to an approximately 90 degree position in reference to the ventral arm. Then a user may configure the adjustable pivot to adjust the device to fit his particular size and fit preference. After the penis is placed onto the ventral arm, the dorsal arm may thereafter be closed onto the penis and a latch arrangement is used to secure the ventral arm to the dorsal arm by placing the head of the latch arrangement through an insert area and into a matching recess section at the end of the dorsal arm. The dorsal and ventral arms should generally be parallel and the user should feel compression once the control device is closed. In some embodiments, a fine adjustment knob, threaded cap, or swivel head, may be rotated to obtain fine tuning and adjustment. The above configuration in use is one example of many.

Embodiments of the invention will now be described in more detail. With reference to FIGS. 1-4, an illustrative male urinary incontinence control device 100 includes a dorsal arm 102 and a ventral arm 104 for applying pressure, or counter pressure, to any area of the penis containing the lateral superficial veins. The ventral arm 104 is configured for application of pressure to the spongy urethra along the ventral surface of the penis. Attached to the dorsal arm 102 are one or more dorsal pads 106, and attached to the ventral arm 104 are one or more ventral pads 108 designed for direct contact with a penis. While the dorsal pads 106 and ventral pads 108 are preferred for patient comfort, some embodiments of the invention may not have such pads.

Figure 1B:
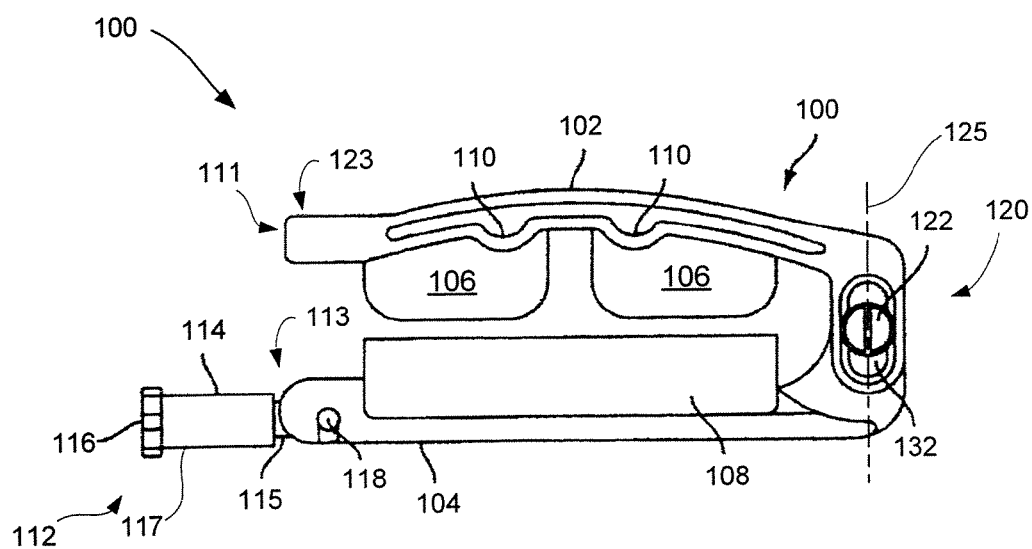
FIG. 1B depicts a right side view of the device of 1A in the same configuration.
Figure 3A:
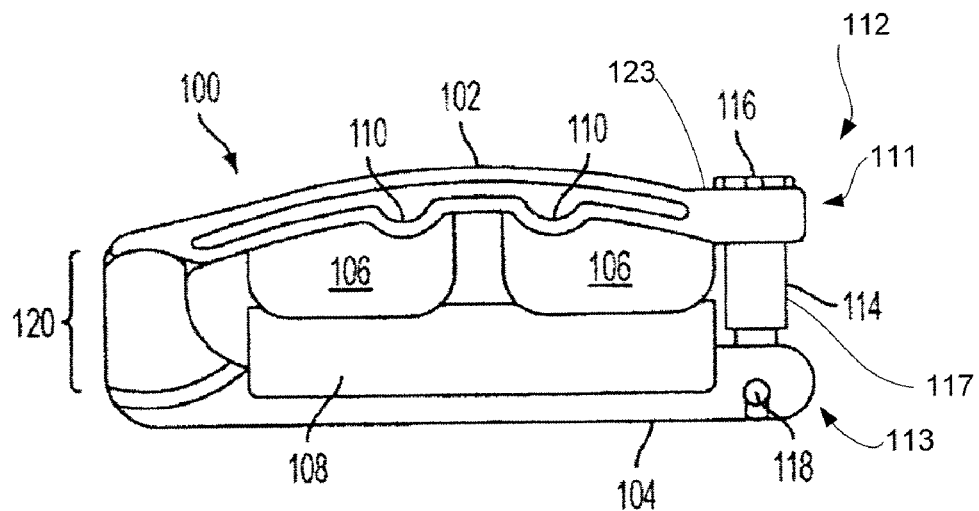
FIG. 3A depicts a left side view of the device of FIG. 1A in a closed and latched configuration.
Figure 3B:
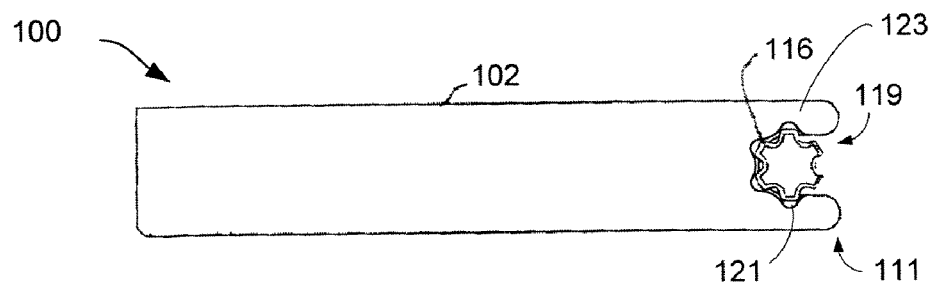
FIG. 3B depicts a top view of the device of FIG. 1A in the same configuration as in FIG. 3A.
Figure 3C:
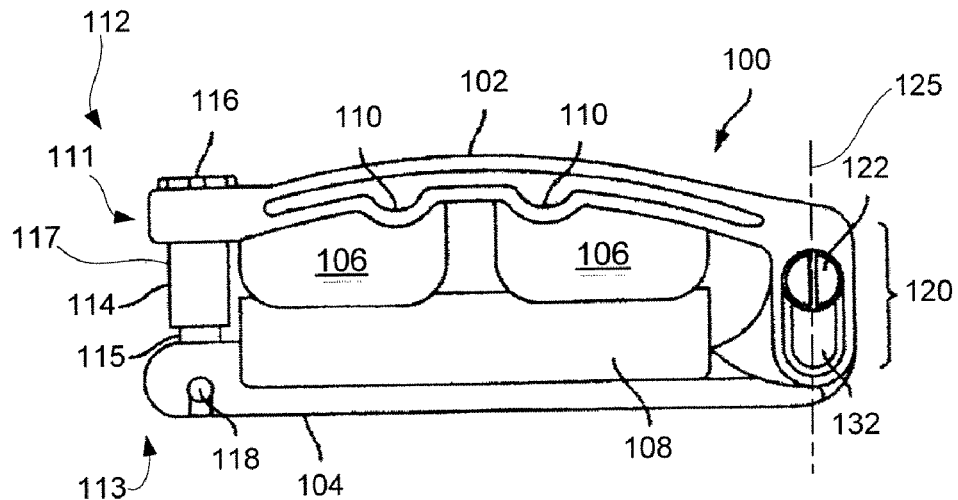
FIG. 3C depicts a right side view of the device of FIG. 1A in the same configuration as in FIG. 3A.
Figure 4A:
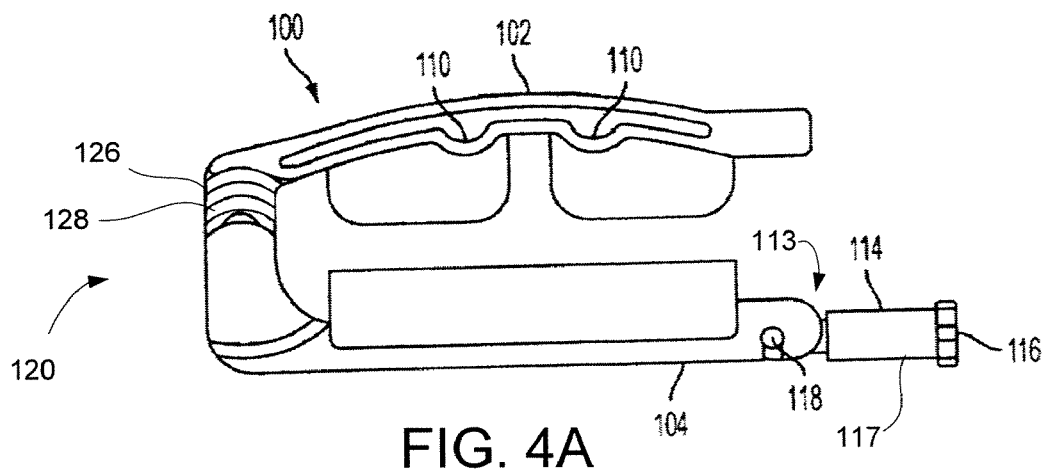
FIG. 4A depicts a left side view of a male incontinence device according to an embodiment of the invention in a closed but unlatched configuration.
Figure 4B:
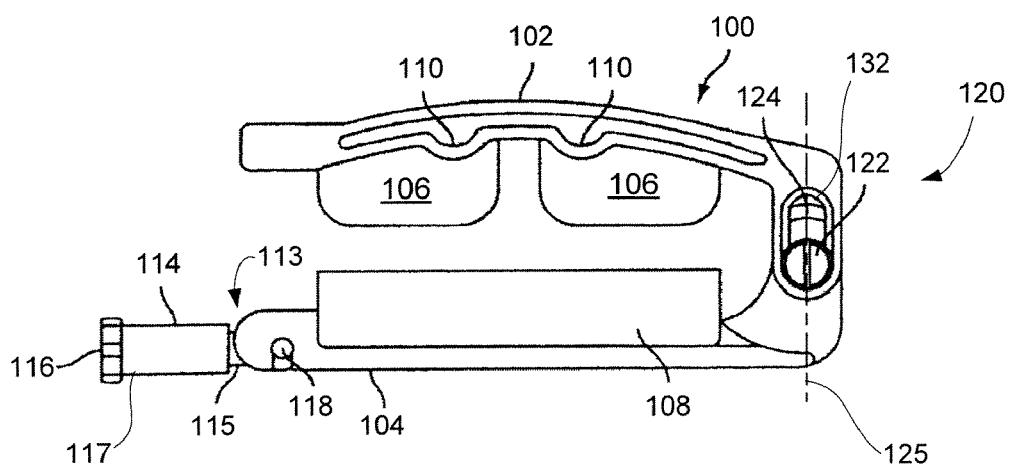
FIG. 4B depicts a right side view of the device of 4A in the same configuration.

The dorsal arm 102 and the ventral arm 104 may be connected to one another at one end by an adjustable hinge mechanism 120 that allows the device 100 to be changed from a closed position such as those shown in FIGS. 1, 3 and 4 to an open position such as that shown in FIG. 2. A latch arrangement 112 at the opposite end of the dorsal and ventral arms 102, 104 is configured to selectively secure the device 100 in the selected closed position.

The adjustable hinge 120 is configured so that the dorsal arm 102 may be freely pivoted relative to the ventral arm 104 about a pivot 122 between a relatively closed position as shown in FIG. 1 and the open position shown in FIG. 2. The adjustable hinge 120 may be further configured so that the position of the pivot 122 relative to the dorsal arm 102 may be adjusted along a dorsal-to-ventral axis 125. Adjustment along this axis 125 allows the closed position spacing between the dorsal arm 102 and the ventral arm 104 to be varied to account for various penis size differences. This spacing may be referred to as the variable height or width of the control device. This ability for varying, but fixed, degrees of separation provides enhanced performance and improved comfort over prior art devices.

In the illustrated device 100, the adjustable hinge 120 comprises an adjustable "channel lock" mechanism. As best shown in FIG. 2 in which the ventral and dorsal pads 106, 108 are not shown, the dorsal arm 102 is formed with a clamping portion 103 and a hinge portion 105 extending at an angle from one end of the clamping portion 103. Similarly, the ventral arm 104 is formed with clamping portion 107 and a hinge portion 109 extending at an angle from one end of the clamping portion 107. The pivot 122 may be a headed pin or similar device attached to the hinge portion 109 of the ventral arm 104 and disposed through a slot 132 in the hinge portion 105 of the dorsal arm 102. The slot 132 is aligned with the axis 125. The channel lock feature may be provided by an arcuate lip 124 disposed on the end of the hinge portion 109 of the ventral arm 104 in combination with corresponding arcuate grooves 126, 128, 130 disposed on the hinge portion 105 of the dorsal arm 102. When in the open position shown in FIG. 2, the pivot 122 may be moved freely along the axis 125 within the slot 132. In order to move the dorsal arm 102 into a closed position, however, the pivot must be positioned so that the arcuate lip 124 can be inserted into one of the arcuate grooves or channels 126, 128, 130. Once the pivot 122 has been so positioned and the dorsal arm 102 pivoted into a closed configuration, the disposal of the arcuate lip 124 within the selected channel prevents movement of the pivot 122 within the slot 132, thereby establishing a fixed height or spacing between the dorsal arm 102 and the ventral arm 104.

The change in height is illustrated by a comparison of FIGS. 1, 3 and 4. FIG. 1 illustrates the device 100 in a configuration wherein the arcuate lip 124 is disposed in the middle channel 128, thereby establishing an intermediate spacing of the dorsal arm 102 and the ventral arm 104. FIG. 3 illustrates the device 100 in a configuration wherein the arcuate lip 124 is disposed in the highest channel 126, thereby establishing a minimum spacing of the dorsal arm 102 and the ventral arm 104. FIG. 4 illustrates the device 100 in a configuration wherein the arcuate lip 124 is disposed in the lowest channel 130, thereby establishing a maximum spacing of the dorsal arm 102 and the ventral arm 104.

It will be understood by those of ordinary skill in the art that the incontinence control device 100 is not limited to a particular number of height adjustments. Using the channel lock mechanism, any number of channels may be used. The more channels used, the greater the flexibility of the device to accommodate a variety of users.

It will further be understood by those of ordinary skill in the art that the positioning of the arcuate lip 124 and the channels 126, 128, 130 could be reversed without departing from the scope of the invention; that is, the arcuate lip 124 could be disposed on the dorsal arm 102 and the channels 126, 128, 130 could be disposed on the ventral arm 104.

The operation of the adjustable hinge 120 can be summarized through a review of FIGS. 1, 2 and 4. From the closed position shown in FIG. 1, the dorsal arm 102 may be pivoted away from ventral arm 104 (counterclockwise in FIG. 1A) to an open position in which the arcuate lip 124 is no longer disposed in the middle channel 128. The ventral arm 102 may then be translated relative to the dorsal arm 104 so that the pivot 122 moves along the axis 125 to the position shown in FIG. 2. In this position, the arcuate lip 124 may be aligned with the lowest channel 130. The dorsal arm 102 may then be pivoted toward the ventral arm 104 (clockwise in FIG. 2A) to the closed position shown in FIG. 4 wherein the arcuate lip 124 is disposed within the lowest channel 130, thereby establishing the maximum spacing between the ventral arm 102 and the dorsal arm 104.

While the lip 124 is generally portrayed as an arced protrusion extending from the hinge portion 109 of the ventral arm 104, the term "lip" is meant to convey a broader spectrum of potential sizes and shapes that would satisfy the function of the device, which is to allow height adjustment through insertion in and engagement with various channels. For example, the lip 124 may alternatively be formed as a post or similar protrusion capable of sliding into a channel section and securing the spacing between the ventral arm 104 and the dorsal arm 102.

It can be seen that by locking the lip 124 into the first (uppermost) channel 126, the tightest possible fit for the control device 100 is achieved. This fit would be preferable for smaller penis sizes, or for patients desiring more pressure placed upon the urethra for greater control over urinary release. When the lip 124 is locked into the second (intermediate) channel 128, an intermediate width or height position is achieved as depicted. Finally, within these exemplary embodiments, the greatest distance between ventral arm 104 and dorsal arm 102 is achieved when the lip 124 is inserted and locked into position in the third (lowermost) channel 130.

While the device 100 is shown with an adjustable hinge 120 having three height positions, one skilled in the art would recognize that any number of adjustment positions may be achieved. In the illustrated embodiment, any plurality of channels may be used to achieve the intended purpose of the control device. Likewise, two or more lip sections could be employed to interlock with the multiple channel sections.

The incontinence control device 100 includes a latch arrangement 112 that is configured to secure and maintain the device in a selected closed position. The latch arrangement 112 may include any form of latch that provides for easy attachment and detachment of the free ends of the dorsal and ventral arms 102, 104. In particularly effective embodiments of the invention, the latch arrangement 112 allows for adjustment of the spacing between the free end 111 of the dorsal arm 102 and the free end 113 of the ventral arm 104. In the illustrated embodiment, the latch arrangement 112 provides this adjustability through the use of a latch member 117 comprising an extensible rod and cap arrangement. Specifically, the latch member 117 comprises a cap 114 and a pivot member 115 pivotably attached to the free end 113 of the ventral arm 104 by a pivot pin 118. The pivot pin 118 may be integrally formed with the pivot member 115 or may be a separate component.

The latch member 117 may be configured so that it can extend beyond the upper surface 123 of the dorsal arm 102 at its free end 113. The ventral arm 104 has a slot 119 at its free end 113 that may be sized to receive the latch member 117 therein. The cap 114 includes a head 116 having a diameter larger than the width of the slot 119 and may be configured to engage the upper surface of the dorsal arm 102 adjacent the slot 119 as discussed in more detail below.

Figure 5A:
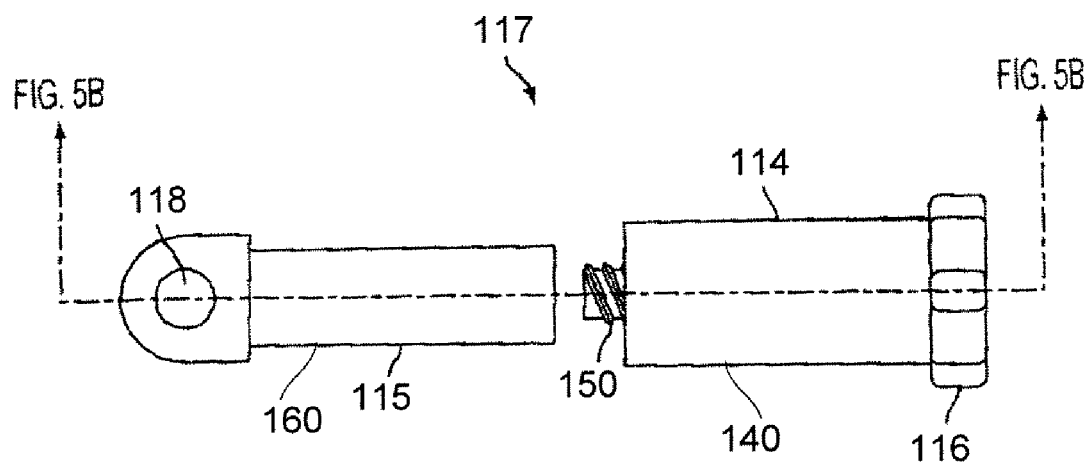
FIG. 5A is a side view of an extensible latch member that may be used in male incontinence devices of the invention.
Figure 5B:
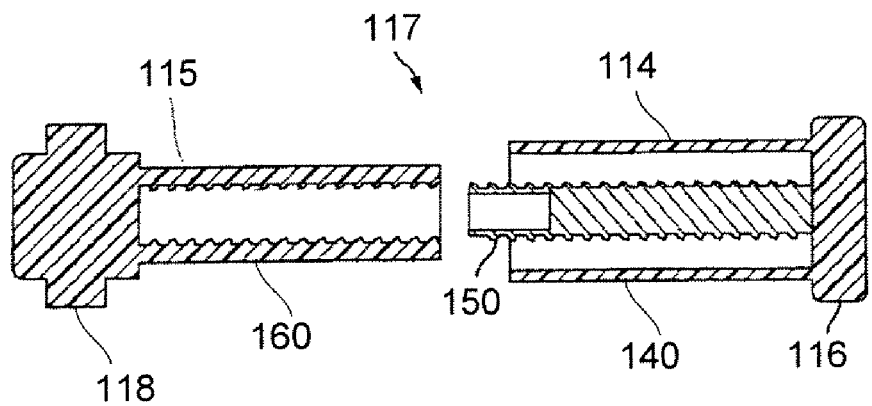
FIG. 5B is a cross sectional view of the extensible latch member of FIG. 5A.

The cap 114 and pivot member 115 each comprise complementary threaded portions so that the cap 114 can be threaded to the pivot member 115. This allows the overall length of the combined cap 114 and pivot member 115 to be adjusted. It will be understood by those of ordinary skill in the art that the thread configurations of the cap 114 and pivot member 115 may take a variety of forms. In one embodiment (not shown), the pivot member 115 may simply be formed as a threaded rod and the cap 114 internally threaded to receive and engage the threaded rod. In another embodiment, illustrated in FIG. 5, the cap 114 has an annular sleeve 140 in which may be disposed a threaded rod 150. The pivot member 115 includes an annular portion 160 that fits within the annular sleeve 140 of the cap 114 and may be internally threaded to receive and engage the threaded rod 150.

The cap head 116 may be shaped to facilitate the rotation of the cap 114 relative to the pivot member 115 to adjust the length of the overall latch member 117. The head 116 may also be configured to engage the upper surface 123 of the dorsal arm 102. In a preferred embodiment, the upper surface 123 of the dorsal arm 102 may have a recessed area 121 configured to receive the cap head 116. The cap head 116 and the recessed area 121 may be shaped in a complementary fashion so that when the cap head 116 has been received by the recessed area 121, the cap head 116 is prevented from rotating. This assures that when the device 100 is secured in a closed position by the latch member 117, the length of the latch member 117 and, thus, the spacing between the free end 111 of the dorsal arm 102 and the free end 113 of the ventral arm 104 cannot be inadvertently increased while the device is being worn.

To use the latch member 117 to latch the closed device 120, the cap 114 may be rotated to lengthen the latch member 117 so that the cap head 116 will extend beyond the upper surface 123 of the dorsal arm 102. The latch member 117 may then be rotated so that the cap 114 can be received into the slot 119. The cap 114 may then be rotated in the opposite direction to shorten the length of the latch member 117 so that the cap head 116 engages the upper surface 123 of the dorsal arm 102.

Once the latch member 117 is in place and the cap head is in engagement with the dorsal arm 102, the latch member 117 can be used as a fine adjustment mechanism. The user may adjust the spacing, and corresponding tightness, between the dorsal arm 102 and the ventral arm 104 at their latched free ends by turning the cap 114 to further shorten the length of the latch member 117. Conversely, turning the cap 114 in the opposite direction lengthens the latch member 117, which loosens the device. It will be understood that in embodiments having dorsal and ventral pads 106, 108, the pads 106, 108 are compressed when the device is put in place. This compression produces a biasing force that tends to push the ventral and dorsal arms 102, 104 apart, which assists in securing the latch 117 member in place. When adjusting the fit of the device 100, the user may temporarily increase the compression of the pads 106, 108 by reducing the spacing between the ventral and dorsal arms 102, 104. The reduced spacing allows the length of the latch member 117 to be adjusted. The user can then release the ventral and dorsal arms 102, 104 to adopt the spacing set by the latch member 117.

It will be understood that the above-described latching mechanism could also be reversed, with the slot 119 formed in the ventral arm 104 and the latch member 117 pivotably attached to the dorsal arm 102.

The control device 100 may comprise cushioning material on the facing surfaces of either or both of the dorsal and ventral arms 102, 104. In some embodiments, the device 100 includes one or more dorsal cushions 106 attached to the lower surface of the dorsal arm 102 and one or more ventral cushions 108 attached to the upper surface of the ventral arm 104.

Figure 6:
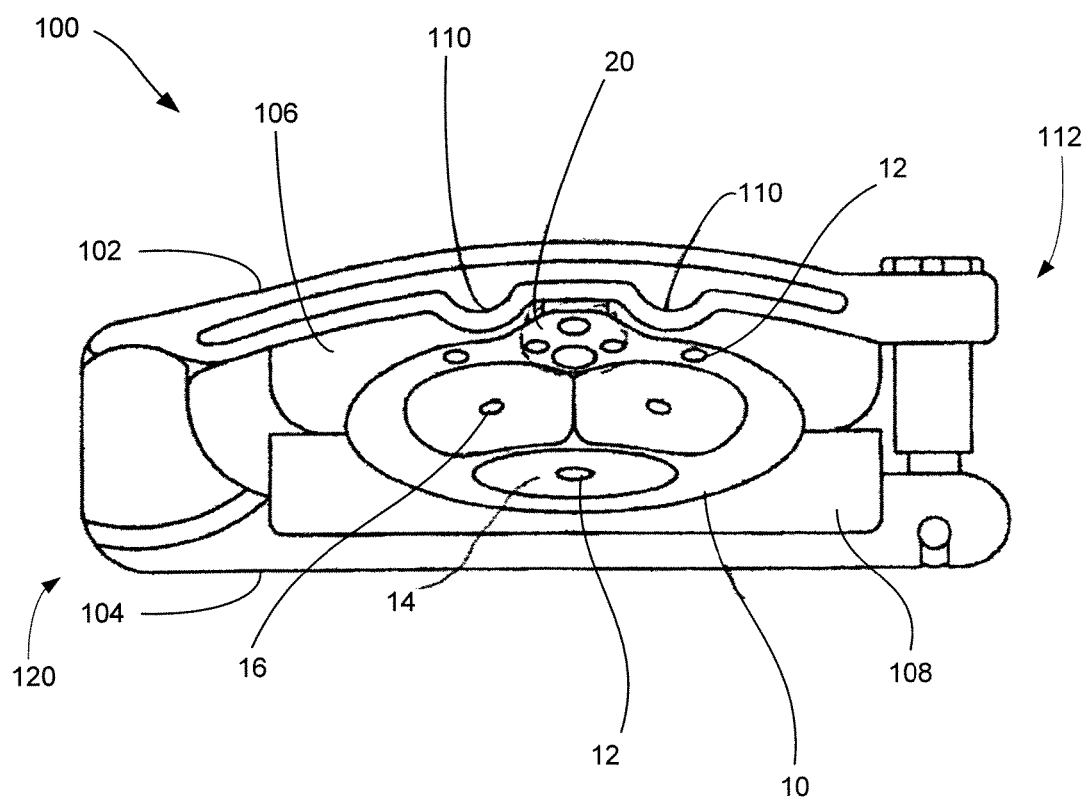
FIG. 6 is a cross sectional view of a penis to which a male incontinence device according to an embodiment of the invention has been applied.

The control device 100 may comprise a plurality of dorsal projections 110 extending ventrally from the lower surface of the dorsal arm 102. These projections are configured so that the pressure applied by the dorsal arm 102 is distributed in a predetermined manner. The dorsal projections 110 may be generally arcuate ridges as shown in FIGS. 1-4. In a preferred embodiment, the dorsal projections 110 and the dorsal cushions 106 are configured so as to reduce pressure upon the lateral superficial veins while maintaining sufficient overall pressure to constrict the urethra. Use of these projections accordingly may assist in maintaining blood flow throughout the penis. FIG. 6 illustrates the positioning of the dorsal projections and the dorsal cushions relative to the structures of a user's penis 10. In particular, one of ordinary skill in the art can see the pressure applied relative to the urethra 12 and the corpus spongiosum 14, the central dorsal vascular group 20, the deep arteries 16, and the lateral superficial veins 12.

To use the male incontinence control device 100 of the invention, a user places the device 100 in an open configuration in which the arms 102, 104 are spread at an angle sufficient to allow placement of the user's penis between the arms 102, 104. The control device 100 may then be placed about the penis and the arms 102, 104 rotated relative to one another toward a closed configuration so that the ventral arm 104 engages the ventral surface of the penis and the dorsal arm 102 engages the dorsal surface of the penis. The user may then further rotate the dorsal and ventral arms 102, 104 to apply a compressive force to the penis. When a desired compressive force has been established, the latch arrangement 112 may be engaged to secure the free ends of the ventral and dorsal arms to one another, thereby preventing the ventral and dorsal arms 102, 104 from separating from the closed configuration. This may be accomplished, in part, by adjusting the length of the latch member 114. Once the latch member 114 is in place, further adjustment of the latch member length may be used as a fine adjustment of the fit of the device. The device 100 may be removed by disengaging the latch arrangement 112 and rotating the dorsal and ventral arms 102, 104 toward the open configuration.

Prior to placement on the user's penis, the spacing between the hinge end of the dorsal arm clamping portion 103 and the ventral arm clamping portion 107 may be adjusted by rotating the dorsal and ventral arms 102, 104 to an angle sufficient to disengage the lip 124 from a previously selected channel 126, 128, 130. The user may then adjust the position of the pivot 122 to select the channel that will produce the spacing desired by the user. With the pivot so-positioned, the dorsal and ventral arms 102, 104 may then be rotated toward the closed position, thereby causing the lip 124 to be received into the selected channel.

The primary structures of the male incontinence control devices disclosed herein may be comprised of any suitable medical grade material. Preferable materials may provide suitable rigidity and resiliency while being easy to clean or sterilize. The cushioning materials of the present invention may be comprised of a foam, a closed or open cell foam, or any similar material providing the advantages discussed herein. The cushions may be secured to each arm through an adhesive, strapping, or other method known in the art. The shape of the dorsal padding sections and ventral padding sections may vary according to patient comfort or according to minor variations in the structural design of the control device.

While the shape of the clamping portion of the ventral arm in the disclosed embodiments are generally straight, one of skill in the art would recognize that an arc or curved ventral arm may be incorporated. Contrastingly, while the dorsal arm in the disclosed embodiments is generally arced or curved along its length, other embodiments of the invention contemplate a generally straight dorsal arm section.

The male incontinence control devices of the invention may be designed specifically to accommodate most penis sizes. A single device may be have a wide range so as to accommodate a wide variety of sizes. Alternatively, devices may be sized with narrower adjustment ranges. The devices of the invention are optimal for adjustment during times when a penis may be swelling or swollen. The control device of the present invention may generally be placed anywhere along the penis shaft, although placement behind the head of the penis is sometimes preferred.

While the control device herein described is primarily intended for human use, one of skill in the art would understand that the device may also find uses for certain other mammals with certain minor modifications. The embodiments pictured and described herein are merely exemplary or illustrative and in no way meant to improperly limit the scope of the claims that follow. One of skill in the art would understand that minor variations of the present examples are possible without deviating from the spirit of the invention, and such deviations or variations may nonetheless fall within the broader scope of the claims. Further, while the invention contemplates certain preferred embodiments, because the control device claimed herein is a personal use device, individual circumstances and preferences will dictate the best configuration for each individual user of the device.

What is claimed is:

1. A male urinary incontinence control device comprising:
   a dorsal arm comprising a dorsal clamping portion having a hinge end and a free end, the dorsal clamping portion being configured for engaging a dorsal surface of a user's penis;
   a ventral arm comprising a ventral clamping portion having a hinge end and a free end, the ventral clamping portion being configured for engaging a ventral surface of a user's penis;
   an adjustable hinge connecting the hinge end of the dorsal arm clamping portion to the hinge end of the ventral arm clamping portion, the adjustable hinge comprising a pivot fixed to one of the ventral and dorsal arms adjacent its hinge end and about which the other of the ventral and dorsal arms can be selectively rotated between a closed position wherein the dorsal arm clamping portion is in opposition with the ventral arm clamping portion and an open position, the location of the pivot relative to the other of the ventral and dorsal arms being selectively adjustable to establish a desired spacing between the ventral and dorsal arms adjacent their hinge ends when in the closed position; and
   a latch attached to at least one of the ventral arm and the dorsal arm and configured for selectively securing the free end of the dorsal arm to the free end of the ventral arm when the ventral and dorsal arms are in the closed position,
   wherein the dorsal arm, ventral arm, and adjustable hinge are configured so that when the ventral and dorsal arms are in the closed position, they are substantially parallel to one another regardless of the selectively adjusted location of the pivot and the spacing between the ventral and dorsal arms and
   wherein the latch comprises a threaded rod portion and a cap portion that combine to form an extensible latch member having a selectively adjustable length, the extensible latch member being pivotably attached at a first end to one of the dorsal arm free end and the ventral arm free end and having a second end configured for engaging the other of the dorsal arm free end and the ventral arm free end to secure the ventral and dorsal arms are in the closed position.

2. The male urinary incontinence control device of claim 1 wherein the dorsal clamping portion comprises a rigid clamping member having one or more dorsal cushions attached to a ventral surface thereof and the ventral clamping portion comprises a rigid clamping member having one or more ventral cushions attached to a dorsal surface thereof, the dorsal and ventral cushions being configured for distributing pressure from the rigid clamping members to selected areas of a user's penis when the ventral and dorsal arms are in the closed position around the user's penis.

3. The male urinary incontinence control device of claim 2 wherein the dorsal and ventral clamping portions are configured so that when placed around a user's penis in the closed position, the dorsal and ventral clamping portions apply pressure sufficient to constrict urinary flow through the urethra.

4. The male urinary incontinence control device of claim 1 wherein the dorsal clamping portion comprises a plurality of rigid ventral projections integrally formed with the dorsal clamping portion and extending ventrally from a ventral surface of the dorsal arm.

5. The male urinary incontinence control device of claim 4, wherein the rigid ventral projections include a pair of central projections positioned one on either side of a plane passing through a cross-sectional centerline of the penis when the ventral and dorsal arms are engaging the penis in the closed position.

6. The male urinary incontinence control device of claim 1 wherein the adjustable hinge comprises a lip formed adjacent the hinge end of one of the dorsal arm and the ventral arm and a plurality of arcuate channels formed adjacent the hinge end of the other of the dorsal arm and the ventral arm, the relative location of the pivot being adjustable so that the lip may be inserted in a selected one of the arcuate channels when the dorsal and ventral arms are moved from the open position to the closed position, the channel selection establishing the desired spacing.

7. The male urinary incontinence control device of claim 1 wherein the extensible latch member comprises a cap threaded to a pivot member, the cap being configured so that turning the cap in a first direction causes the extensible latch member to lengthen and turning the cap in the opposite direction causes the extensible latch member to shorten.

8. The male urinary incontinence control device of claim 1 wherein the other of the dorsal arm free end has a slot formed therein, the slot being configured to receive a portion of the extensible latch member when the ventral and dorsal arms are in the closed position.

9. A male urinary incontinence control device comprising:
a dorsal arm comprising a dorsal clamping portion having a hinge end and a free end, the dorsal clamping portion being configured for engaging a dorsal surface of a user's penis;
a ventral arm comprising a ventral clamping portion having a hinge end and a free end, the ventral clamping portion being configured for engaging a ventral surface of a user's penis;
hinge means for connecting the hinge end of the dorsal arm clamping portion to the hinge end of the ventral arm clamping portion, the hinge means comprising a pivot fixed to one of the ventral and dorsal arms adjacent its hinge end and about which the other of the ventral and dorsal arms can be selectively rotated between a closed position wherein the dorsal arm clamping portion is in opposition with the ventral arm clamping portion and an open position, and means for selectively adjusting the location of the pivot relative to the other of the ventral and dorsal arms to establish a desired spacing between the ventral and dorsal arms adjacent their hinge ends when in the closed position; and
latch means for selectively securing the free end of the dorsal arm to the free end of the ventral arm when the ventral and dorsal arms are in the closed position,
wherein the dorsal arm, ventral arm, and hinge means are configured so that when the ventral and dorsal arms are in the closed position, they are substantially parallel to one another regardless of the selectively adjusted location of the pivot and the spacing between the ventral and dorsal arms and
wherein the latch means comprises a threaded rod portion and a cap portion that combine to form an extensible latch member having a selectively adjustable length, the extensible latch member being pivotably attached at a first end to one of the dorsal arm free end and the ventral arm free end and having a second end configured for engaging the other of the dorsal arm free end and the ventral arm free end to secure the ventral and dorsal arms are in the closed position.

10. The male urinary incontinence control device of claim 9 wherein the dorsal clamping portion comprises a rigid clamping member having one or more dorsal cushions attached to a ventral surface thereof and the ventral clamping portion comprises a rigid clamping member having one or more ventral cushions attached to a dorsal surface thereof, the dorsal and ventral cushions being configured for distributing pressure from the rigid clamping members to selected areas of a user's penis when the ventral and dorsal arms are in the closed position around the user's penis.

11. The male urinary incontinence control device of claim 10 wherein the dorsal and ventral clamping portions are configured so that when placed around a user's penis in the closed position, the dorsal and ventral clamping portions apply pressure sufficient to constrict urinary flow through the urethra.

12. The male urinary incontinence control device of claim 9 wherein the dorsal clamping portion comprises a plurality of rigid ventral projections integrally formed with the dorsal clamping portion and extending ventrally from a ventral surface of the dorsal arm.

13. The male urinary incontinence control device of claim 12, wherein the rigid ventral projections include a pair of central projections positioned one on either side of a plane passing through a cross-sectional centerline of the penis when the ventral and dorsal arms are engaging the penis in the closed position.

14. The male urinary incontinence control device of claim 9 wherein the hinge means comprises a lip formed adjacent the hinge end of one of the dorsal arm and the ventral arm and a plurality of arcuate channels formed adjacent the hinge end of the other of the dorsal arm and the ventral arm, the relative location of the pivot being adjustable so that the lip may be inserted in a selected one of the arcuate channels when the dorsal and ventral arms are moved from the open position to the closed position, the channel selection establishing the desired spacing.

15. The male urinary incontinence control device of claim 9 wherein the extensible latch member comprises a cap threaded to a pivot member, the cap being configured so that turning the cap in a first direction causes the extensible latch member to lengthen and turning the cap in the opposite direction causes the extensible latch member to shorten.

16. The male urinary incontinence control device of claim 9 wherein the other of the dorsal arm free end has a slot formed therein, the slot being configured to receive a portion of the extensible latch member when the ventral and dorsal arms are in the closed position.

17. A method of using a male urinary incontinence control device comprising a dorsal arm, a ventral arm and a latch, the dorsal and ventral arms each having a hinge end and a free end and being connected to one another at the hinge ends by an adjustable hinge configured to allow relative rotation of the ventral and dorsal arms between a closed configuration in which the ventral and dorsal arms are substantially parallel and an open configuration and to allow selective adjustment of a closed position spacing between the ventral and dorsal arms, the dorsal clamping portion comprising a plurality of rigid ventral projections extending ventrally from a ventral surface of the dorsal arm, and the latch comprising a threaded rod portion and a cap portion that combine to form an extensible latch member having a selectively adjustable length and being configured for selectively securing the free end of the dorsal arm to the free end of the ventral arm when the ventral and dorsal arms are in the closed position, the method comprising:

with the dorsal and ventral arms in the open configuration, positioning the dorsal arm to engage a dorsal surface of a user's penis;

selecting a desired closed position spacing;

rotating the ventral arm relative to the dorsal arm toward the closed position so that the ventral arm engages a ventral surface of the user's penis;

further rotating the ventral arm relative to the dorsal arm so that a compressive force is applied to the user's penis by the ventral and dorsal arms;

adjusting the length of the extensible latch member; and securing the free end of the dorsal arm to the free end of the ventral arm with the latch.

18. The method of claim 17, wherein the adjustable hinge comprises a lip formed adjacent the hinge end of one of the dorsal arm and the ventral arm and a plurality of arcuate channels formed adjacent the hinge end of the other of the dorsal arm and the ventral arm and wherein the action of selecting a desired closed position spacing includes adjusting a position of the dorsal arm hinge end relative to the ventral arm hinge end so that the lip may be inserted in a selected one of the arcuate channels when the ventral arm is rotated from the open position toward the closed position, the channel selection establishing the desired closed position spacing.

* * * * *